US011484445B1

(12) United States Patent
Garner

(10) Patent No.: US 11,484,445 B1
(45) Date of Patent: Nov. 1, 2022

(54) TEMPERATURE VARIANT STOCKINGS

(71) Applicant: Carol Garner, Mason, OH (US)

(72) Inventor: Carol Garner, Mason, OH (US)

( * ) Notice: Subject to any disclaimer, the term of this patent is extended or adjusted under 35 U.S.C. 154(b) by 805 days.

(21) Appl. No.: 15/853,851

(22) Filed: Dec. 25, 2017

Related U.S. Application Data

(63) Continuation-in-part of application No. 14/953,418, filed on Nov. 29, 2015.

(60) Provisional application No. 62/123,824, filed on Dec. 1, 2014.

(51) Int. Cl.
| | |
|---|---|
| *A61F 13/08* | (2006.01) |
| *A41B 11/00* | (2006.01) |
| *A61F 7/03* | (2006.01) |
| *A61F 13/00* | (2006.01) |
| *A01N 59/06* | (2006.01) |
| *A01N 59/16* | (2006.01) |

(Continued)

(52) U.S. Cl.
CPC .............. *A61F 13/08* (2013.01); *A01N 59/06* (2013.01); *A01N 59/16* (2013.01); *A41B 11/003* (2013.01); *A41B 11/005* (2013.01); *A61F 7/03* (2013.01); *A61F 13/00991* (2013.01); *A41B 2400/34* (2013.01); *A61F 2007/0043* (2013.01); *A61F 2007/0045* (2013.01); *A61F 2007/0046* (2013.01); *A61F 2007/0233* (2013.01)

(58) Field of Classification Search
CPC ................ A61F 13/08; A61F 13/00063; A61F 13/00995; A61F 13/061; A61F 13/107; A61F 5/0109; A61F 13/10
See application file for complete search history.

(56) References Cited

U.S. PATENT DOCUMENTS 3,900,035 A * 8/1975 Welch ....................... A61F 7/10
607/108
2008/0249454 A1* 10/2008 Mills ....................... A61F 13/08
602/63

(Continued)

FOREIGN PATENT DOCUMENTS

KR     2006070619 A *  6/2006    ........... A41B 11/007

OTHER PUBLICATIONS

No Author Named, "Hot Compression Stockings That Are Not Too Hot for the Summer", Jun. 12, 2012, http://www.compressionstockings-site.com/which-compression-stockings . . . , last visited Jan. 6, 2017.

(Continued)

*Primary Examiner* — Ophelia A Hawthorne

(57) ABSTRACT

Temperature variant compression stockings are three-in-one stockings that address needs both in the sports world and the medical field. The temperature variant stockings may help cool the skin while exerting a desired compressive force; another version of the temperature variant stockings may actually retain heat while also exerting a desired compressive force. The stockings are available where the temperature variant components are in contact with the user's skin while the compression yarns are knitted onto the outside of the stocking. A style is also available with alternating strips, with either the cooling yarns or the heat retaining yarns running vertically and parallel to strips of compression yarns. Antimicrobial particles are infused into the cooling or heating yarns to guard again infections.

3 Claims, 4 Drawing Sheets

(51) Int. Cl.
  *A61F 7/00* (2006.01)
  *A61F 7/02* (2006.01)

(56) References Cited

U.S. PATENT DOCUMENTS

2011/0214315 A1* 9/2011 Mayer .................. A61F 5/14
  36/140
2013/0133353 A1* 5/2013 Araujo ............... A41D 13/0055
  62/331

OTHER PUBLICATIONS

Compression stockings, www.amazon.com/compression-graduated- . . . , last visited Feb. 17, 2017.
Ifai, Garmatex Introduces Ice Skin (TM) Cooling Fabric, Sep. 8, 2014, last visited Mar. 5, 2018.

* cited by examiner

TEMPERATURE VARIANT STOCKINGS

CROSS-REFERENCE TO RELATED APPLICATIONS

This application is a Continuation-in-Part Application that claims the benefit of U.S. Utility application Ser. No. 14/953,418, filed Nov. 29, 2015, having the title "Cool Compression Stockings," by Carol Garner, which claims the benefit of U.S. Provisional Application No. 62/123,824, filed Dec. 1, 2014, having the title "Cool Compression Stockings," by Carol Garner, both of which are incorporated herein by reference in their entirety.

FIELD OF DISCLOSURE

The present disclosure relates to compression stockings that relieve a number of uncomfortable conditions that can arise when participating in sports events or during ordinary daily activities for individuals with medical ailments.

BACKGROUND

Compression stockings and orthopedic stockings, particularly when worn to treat medical conditions, are not designed with appearance in mind. Traditionally, compression stockings are unattractive, thus causing embarrassment for those required to wear them. Compression stockings that provide a cooling effect or a warming effect to the user's leg are beneficial for both sports enthusiasts and for those with circulation disorders. Compression stockings made from a fabric with an antimicrobial particle may reduce odor caused from excessive perspiration generated during sports activities. Compression stockings made from a fabric with an antimicrobial particle may also reduce the incidence of bacterial infections that could arise when users with compromised skin conditions are required to wear compression stockings around the clock for health reasons.

BRIEF SUMMARY

In a current embodiment, compression stockings with cooling properties have a cooling fabric embedded with antimicrobial particles. Cool compression stockings exert pressure along a foot surface and lower leg surface to provide support and enhance circulation. A cooling component with wicking properties in the compression stocking's fabric produces a cooling effect when the fabric is in contact with the skin. Likewise, compression stockings with thermal properties produce a warming effect when the fabric is in contact with the skin. When cool or thermal compression stockings also feature fabric containing antimicrobial particles, the likelihood of bacterial growth is reduced.

DETAILED DESCRIPTION

Figure 1A:
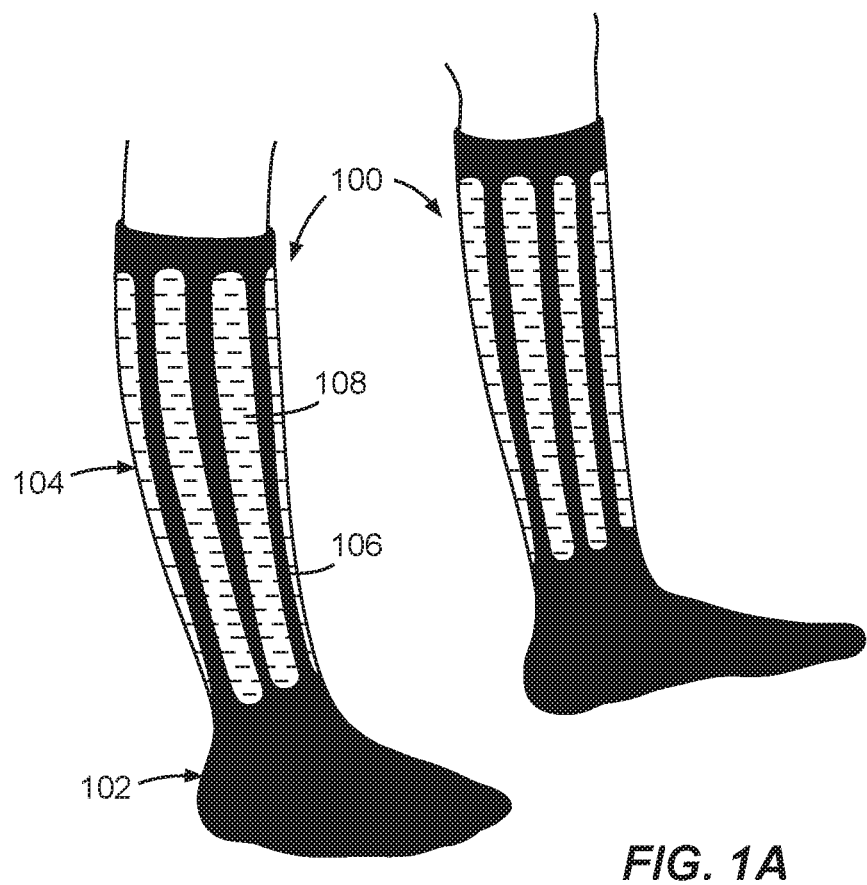
FIG. 1 shows one embodiment of temperature variant compression stockings. In this view, the compression stocking is a cool compression embodiment with cooling strips that run vertically from a neck portion of a foot to the area of a leg just below a knee. The cooling strips may be replaced with a thermal fabric in a thermal compression embodiment.

Reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

Although exemplary embodiments are shown and described, it will be clear to those of ordinary skill in the art that a number of changes, modifications, or alterations to the disclosure as described may be made. An all-cotton or all polyester fabric could be used in the place of the elasticized nylon cotton blend portion of the compression stocking. Cooling fabric technology and thermal fabric technology are rapidly developing fields as is the technology that teaches how to infuse gold, silver, jade or other antimicrobial particles into fabrics. One skilled in the art of compression stockings will appreciate that a number of permutations of these technologies can be added and included without altering the terms described and claimed herein.

Currently, numerous compression stockings exist. However, these stockings suffer from various drawbacks. In many instances, compression stockings worn for medical purposes are white or flesh-colored and call attention to one's impairment. The disclosed product and method provide an alternative approach that remedies the various drawbacks existent in those previously proposed products and methods.

As defined herein, the term "antimicrobial nanoparticle" refers to particles that are used for a variety of different antimicrobial applications. For example, silver compounds and silver ions have been known to show antimicrobial properties and have been used in a wide range of applications. Silver nanoparticles have an antibacterial effect, and are also used in a variety of consumer products such as workout exercise clothing to reduce or to prevent the odor that builds up when users perspire. Antimicrobial nanoparticles may also refer to jade and metal salts of gold, zinc and titanium, but this list is not exclusive as it also may include other antimicrobial agents including charcoal. The term "antimicrobial" refers to the elimination of bacterial and fungal organisms.

As defined herein, the term "compression sleeve" refers to an open-ended tubular garment that is designed to help prevent the occurrence of, and to guard against further progression of certain medical conditions. Athletes may also wear compression sleeves in order to enhance performance during sports practices and contests. Compression sleeves are worn around the arm, foot and leg, compressing the limbs. Compression sleeves may also include support hose and elastic leggings where the foot portion has been removed. Herein, the compression fabrics selected may exert anywhere from approximately 8-15 mmHg (millimeters of mercury) up to approximately 40-50 mmHg of pressure.

As defined herein, the term "compression stocking" refers to specialized hosiery, designed to help prevent the occurrence of, and to guard against further progression of certain medical conditions. Athletes may also wear compression stockings in order to enhance performance during sports practices and contests. Compression stockings are worn around the foot and leg, compressing the limbs. Compression stockings may also include support hose and elastic leggings. Herein, the compression fabrics selected may exert anywhere from approximately 8-15 mmHg (millimeters of mercury) up to approximately 40-50 mmHg of pressure.

As defined herein, the term "fabric" refers to the basic structure of an object, namely a textile including woven and knitted materials. The term "fabric" also refers to fibers that are used to make the fabric.

As defined herein, the term "nanoparticle" refers to particles with sizes between approximately 1 and 200 nanometers, but this range is not limited to between 1 and 200 nanometers.

As defined herein, the term "sleeve" refers to a tubular part designed to fit over another part. Thus the term "sleeve" may refer to an open-ended tubular garment designed to fit over an arm or a leg. Any properties attributed to a "stocking" herein may be used to describe properties in a "sleeve".

As defined herein, the term "stocking" refers to a close fitting covering, usually of a knitted material for the foot and leg. As defined herein, the term "stocking" may also refer to a close-fitted covering, usually of a knitted material, for portions of the leg, originating at or below the knee and terminating at a point on the foot or above the foot.

As defined herein, the term "thermal" refers to a fabric property in a compression stocking that provides a warming effect beyond the heat that the body can generate naturally on its own.

Compression Fabrics

Figure 1B:
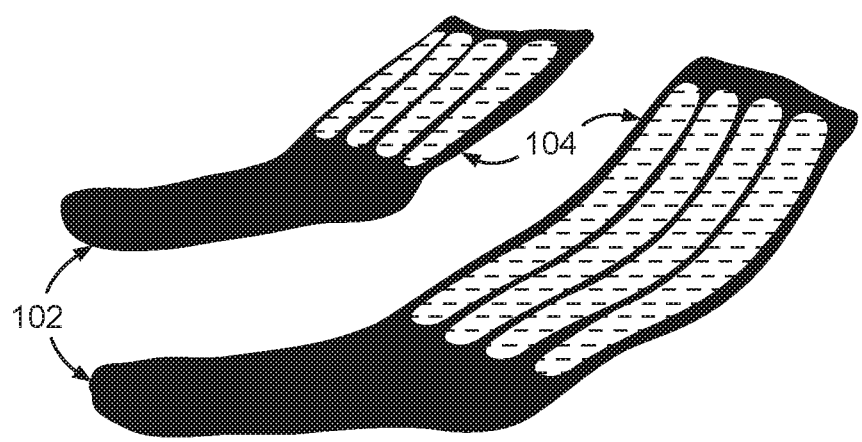

Referring to FIG. 1, the compression stocking is made of an elasticized nylon-cotton blend fabric. A salient feature here is that the stocking is shown in a dark color, rather than a clinical flesh hue or hospital-white color. The dark-colored stocking in this embodiment would go unnoticed and would be acceptable attire with slacks. In another embodiment, colors other than black or white are available. Although some athletic stockings with minimal compression also feature colors and patterns, these colors and patterns are not enjoying widespread use in the medical field.

Referring again to FIG. 1, the elastic materials and threads as well as the elasticity characteristics in the stocking comply with medical compression stocking standards as outlined under RAL-GZ 387 of September 2000. The RAL-GZ 387 Standards govern quality assurance testing of medical compression stockings. These standards were initiated originally to assure best treatment practices for edema and are now enjoying widespread use when treating other medical conditions.

The compression fabric in cool compression stockings or thermal compression stockings may exert a pressure on user's legs anywhere from approximately 8-15 mmHg to approximately 40-50 mmHg.

The 8-15 mmHg range is the lightest form of compression. The lightest form of compression will still energize the user's legs and offer some assistance for tired and achy legs. Enhanced blood circulation is experienced, which helps control swelling. The lightest form of compression is ideal for an athlete.

Relief from minor to moderate swelling, aching, and the occurrence of varicose veins is felt from the mild compression of 15-20 mmHg. Those who are required to sit or stand for long periods of time will see a benefit to a mild compression stocking. Pressure within 15-20 mmHg is sufficient to help prevent deep vein thrombosis for long distance travelers.

Physicians may prescribe a moderate compression stocking where the pressure is between 20-30 mmHg. Stockings in this range of pressure treat a number of mild to moderate medical conditions including chronic varicose veins, edema, and deep vein thrombosis.

Physician supervision is typically involved with compression stockings with pressure ranging from 30-40 mmHg. While providing relief from some of the same conditions as a moderate compression stocking, including chronic varicose veins, edema, and deep vein thrombosis, these stockings are also helpful in healing active venous stasis ulcers.

The 40-50 mmHg pressure is required to treat chronic venous insufficiency, post-thrombotic syndrome and other compromised medical conditions. Compression fabric with 40-50 mmHg is typically used only when prescribed by a physician.

Temperature Variant Fabrics

Those skilled in the art of cooling fabrics will recognize that cooling fabrics exist that wick perspiration from the skin at which time the skin feels cooler. Other cooling fabrics may include cooling elements coupled to a base fabric. For example, jade can be used as a cooling agent. Cooling elements may include cooling gels or polymers or phase change materials. The cooling elements may undergo a chemical or physical change when exposed to moisture, where heat is absorbed in the process. Those skilled in the art of thermal fabrics are aware that fabrics exist that will retain warmth when activated by perspiration. The wicking components of the thermal fabric provide comfort when the heat from the skin and the fabric combine.

Therapeutic cold packs at temperatures lower than the normal temperature of the human body have been used medically for centuries to help reduce pain and swelling. One skilled in the art of cold packs will recognize that cold packs that are shapeable to the contours of a leg and foot over a range of temperatures exist. Currently, the medical application of gel packs restricts the user's mobility, normally confining the user to a chair or bed during use. A flexible therapeutic cold pack attached to a compression stocking may allow for the cooling of portions of a leg or foot that are at risk for heat build up.

Correspondingly, it is well known in the art that fabrics exist that produce superior warming properties. A flexible therapeutic warming pack attached to a compression stocking may allow for the warming of portions of a leg, foot or arm that are at risk due to exposure to the cold weather.

Antimicrobial Properties

Antimicrobials, including antimicrobial nanoparticles, may be added to fabrics to reduce the odor from excessive perspiration build-up as well as to reduce bacterial growth. In one embodiment, jade nanoparticles may be added to the cooling fabric to prevent the likelihood of infection when the compression stockings are in contact with the skin for long periods of time, or when the skin is delicate and tends to break down.

The cooling fabric 104 may also be infused with an antimicrobial particle, including nanoparticles of metal salts of silver, gold, zinc and titanium, but this list is not limited to silver, gold, zinc and titanium as it also may include other antimicrobial agents. Of the four metals disclosed herein and currently used, silver is currently the most widely used. The cooling properties of the nanoparticle jade have also been illustrated to contain antimicrobial properties. Antimicrobials may also be added to thermal fabrics 104.

Cool and Thermal Compression Stockings

Referring to FIG. 1, the cool compression stocking 100 covers the foot 102, and leg 104. In another variation, and referring to FIG. 5A, the cool compression stocking originates at the cuff 214 and terminates at a point just where the foot portion 220 begins. In yet another variation, and referring to FIG. 5B, the cool compression stocking originates at the cuff 214 and terminates at a location on top of a foot 218 at a point where the arch of the bottom of the foot 224 is at its highest point distant from the heel 204 of the foot 224.

Figure 2A:
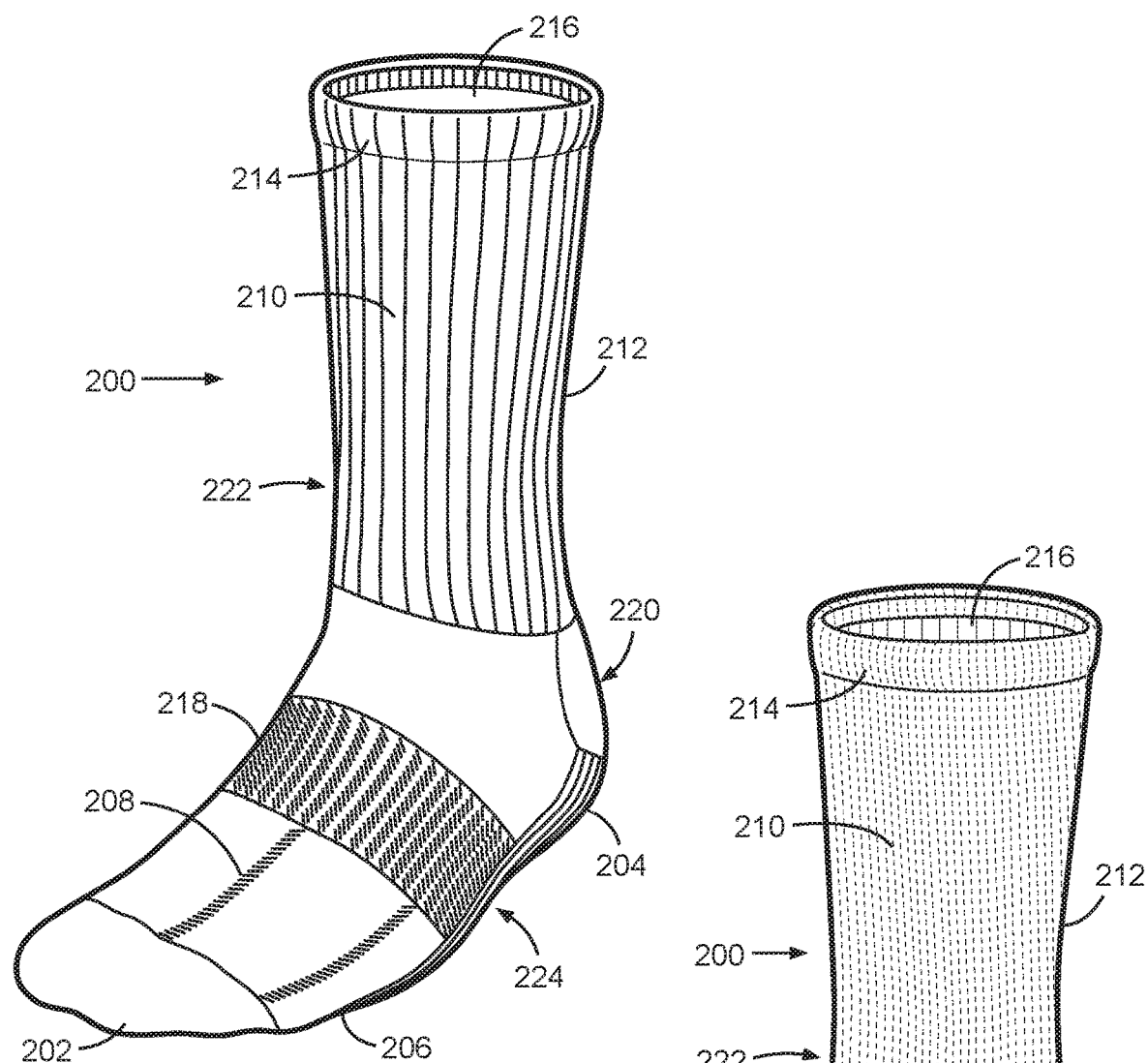
FIG. 2A shows a generic compression stocking that includes cooling properties and antimicrobial particles on an inside surface of the compression fabric. The generic compression stocking could include thermal properties and antimicrobial particles on an inside surface of the compression fabric.
Figure 2B:
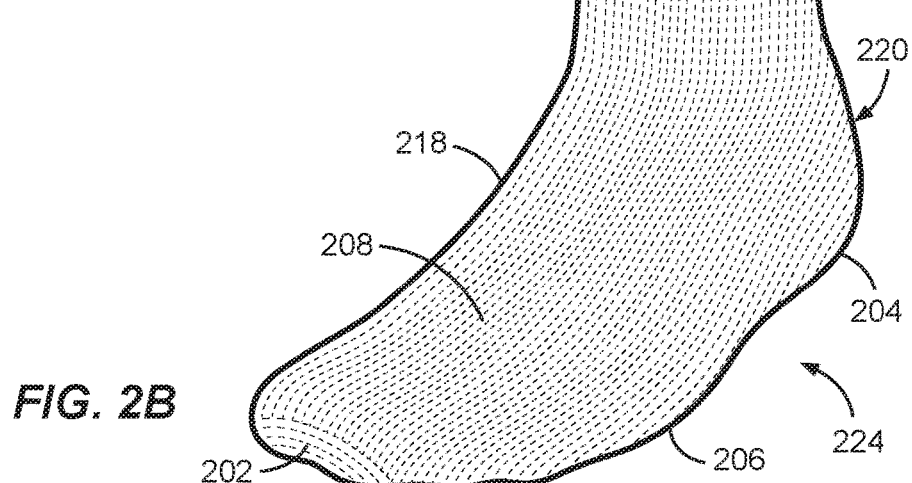
FIG. 2B shows a compression stocking that includes cooling properties and antimicrobial particles on an inside surface of the compression fabric. A thermal embodiment of a compression stocking could include threads with thermal properties and antimicrobial particles on an inside surface of the compression fabric.

As seen in FIG. 1, a compression fabric exerts a select range of pressures along the upper and lower portions of a user's foot 102 and the calf and shin portions of the leg 104. Referring to FIG. 2, increased pressure is applied in the preferred embodiment 200 on the foot 224, on the heel 204, on the top portions 208, 218 and on the bottom portion 206 of the foot 224. Pressure is applied over all portions of the leg 222. Illustrative of the pressure points on the leg 222 are pressure points on the shin 210 and calf 212 portions of the leg. However, the pattern of the compression threads may vary depending on the area of the foot or leg that requires more or less compression.

In one embodiment solely for the cool compression stocking, and referring to FIG. 1, the compression fabric 106 and the cooling fabric 108 are shown in contrasting colors. One such cooling fabric is a polyvinyl alcohol fabric and those skilled in the art of cooling fabrics will recognize that there are numerous variations of cooling fabrics currently in the marketplace.

Figure 3:
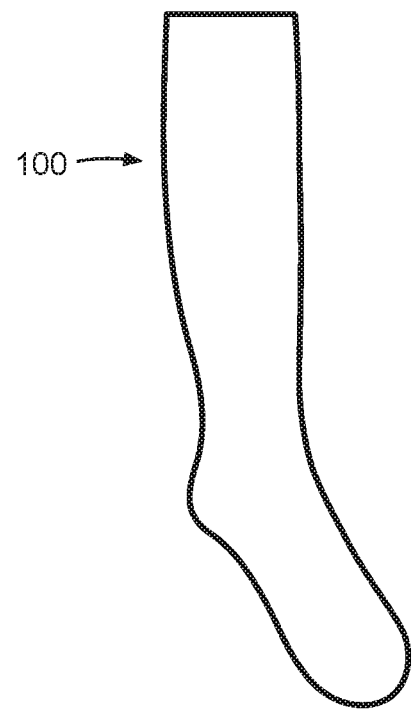
FIG. 3 shows a side view of a compression stocking before modifications are made to add a cooling fabric. The cooling fabric may be replaced by a thermal fabric.
Figure 4:
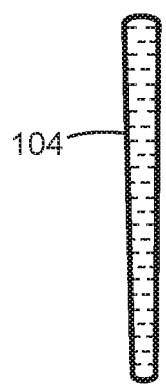
FIG. 4 shows an example of a cooling fabric before it is incorporated into the body of the stocking. A thermal fabric may be incorporated into the body of the stocking in the place of the cooling fabric.

In order to assemble the cool compression stocking in one embodiment and referring to FIG. 3, one begins with a compression fabric 100 shown in FIG. 3 in white. The compression fabric is adapted to receive strips of a cooling fabric 104. For illustrative purposes the cooling fabric 104 is shown in a second color. During the manufacturing process, the compression fabric and cooling fabric may be operatively connected in strips to create the cool compression stocking as shown in FIG. 1. Although in FIG. 3 the stocking 100 and cooling fabric 104 are shown in contrasting colors, in another embodiment, the stocking 100 and fabric 104 may be made with the same color.

Figure 5:
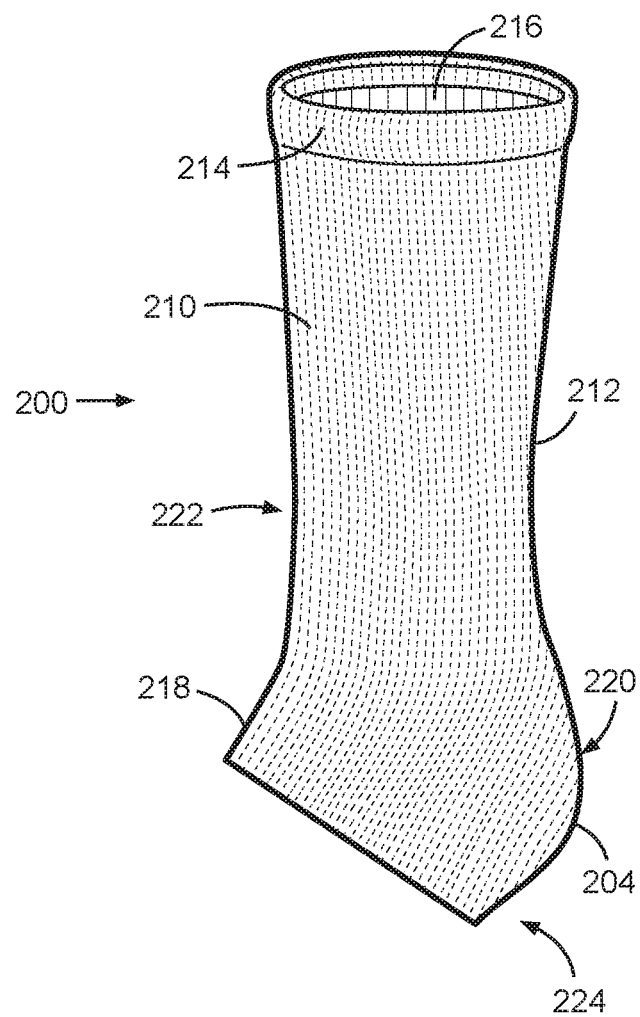
FIG. 5A shows an example of a temperature variant compression stocking that originates at a point just below a knee and terminates at an ankle. If a thermal fabric is used in place of the cooling fabric, the temperature variant stocking as shown may serve as a thermal stocking.
FIG. 5B shows an example of a temperature variant compression stocking that originates at a point just below a knee and terminates at a mid-point of a foot.

In another embodiment, cooling fabric is introduced as the inside layer with the compression fabric as the outside layer of a two layer stocking. The cooling fabric and compression fabric may originate at the cuff 214 of the stocking and terminate at any point in the leg area 222 or at any point in the foot area 224 of the stocking up to and including the toe 202 portions. The style of the two layer cool compression stocking may be modified for comfort or to allow easy access for medical procedures to the foot, as seen in FIG. 5A and FIG. 5B. In another embodiment, and still referring to FIG. 5A and FIG. 5B, the stocking may be made by ordering the cooling threads towards the inside surface 216 and the compression threads towards the outside surface 210.

Alternatively, thermal fabric is introduced as the inside layer with the compression fabric as the outside layer of a two layer stocking. The thermal fabric and compression fabric may originate at the cuff 214 of the stocking and terminate at any point in the leg area 222 or at any point in the foot area 224 of the stocking up to and including the toe 202 portions. The style of the thermal compression stocking may be modified for comfort or to allow easy access for medical procedures to the foot, as seen in FIG. 5A and FIG. 5B. In another embodiment, and still referring to FIG. 5A and FIG. 5B, the stocking may be made by assigning the thermal threads to the inside surface 216 and by assigning the compression threads to the outside surface 210.

In another embodiment, the cooling fabric is actually a fabric that encases cold packs. This cooling fabric is operatively joined to the outside layer of the compression fabric in alternating strips as shown in FIG. 1. The stockings are placed in a refrigerator or freezer until the cold packs reach a clinically designated temperature. Thereafter, the cool compression stockings in this embodiment are worn until the cooling properties of the cold packs are exhausted, refrozen or replaced. When using compression stockings to achieve thermal properties, alternating strips as shown in FIG. 1 can accommodate warming packets.

Two-Layer Cool and Thermal Compression Stockings

In another embodiment, a cool compression stocking 200 is shown as a two-layer stocking. In FIG. 2A an outside surface of the compression fabric is defined by a toe portion 202, a heel portion 204, a top surface 208 of a foot portion and a bottom surface 206 of a foot portion, a heel portion 204, a leg portion showing a calf portion 212 and a shin portion 210, a neck portion 218, a cuff portion 214 and an inside surface 216. The stocking 100 exerts pressure on various portions of a user's foot 202, 204, 206, 208 and leg 212. The shaded areas in FIG. 2A show one embodiment wherein extra pressure is applied to the shaded areas through tightening the elasticity of the fabric in those shaded areas in compliance with RAL-GZ 387 Standards.

In the two-layer embodiment with a compression fabric as the outside layer, the inside surface 216 of the compression fabric operatively receives a cooling fabric. The cooling fabric 104 overlays the inside layer 216 of the compression fabric and is disposed onto the compression fabric in order to construct the stocking. The cooling fabric 104 may also be infused with an antimicrobial particle, including a nanoparticle. Antimicrobial nanoparticles currently used include metal salts of silver, gold, zinc and titanium, but this list is not limited to silver, gold, zinc and titanium as it also may include other antimicrobial agents including jade. Jade is gaining recognition as a nanoparticle of choice as it has not only antimicrobial properties but also is used to reduce the skin temperature.

Alternatively, the compression fabric could receive a thermal fabric. The thermal fabric 104 overlays the inside layer 216 of the compression fabric and is disposed onto the compression fabric in order to construct the stocking. The thermal fabric 104 may also be infused with an antimicrobial particle, including a nanoparticle, most commonly silver.

FEATURES AND BENEFITS

The compression component of cool compression stockings provides leg support during exertion and improves circulation. The cooling feature in the cool compression stockings will ensure a more comfortable experience particularly for those who reside in warmer climates and need to wear compression stockings for health reasons. For those residing in cold climates wanting or needing to spend extended periods of time outdoors or for those who work in cold environments, the warming features of thermal compression stockings will provide the ability to maintain comfort and may reduce the dangers from exposure to cold temperatures. The addition of antimicrobial particles helps prevent infections for those whose health may be immune-compromised or who may have difficulties removing the stockings periodically to allow the skin to breathe. This feature becomes essential for those who are required to wear compression stockings for long periods of time.

The cool compression stocking is modified to accommodate a wide range of needs. For example, after a sprain, medical procedure or surgery, an individual may prefer a compression stocking that terminates above the toes or ankle. Correspondingly, an individual may prefer the comfort of a sleeve that covers fingers, the hand or arm.

Athletes in a number of sports including football, baseball and soccer are required to wear knee-length hose. When athletes compete, especially in warm climates, the cooling effects of cool compression stockings, together with the antimicrobial features, will provide more comfort from heat build-up and also reduce odor-forming bacteria due to excess perspiration.

What is claimed is:

1. A temperature variant stocking comprising:
   a foot portion, wherein the foot portion has a top surface and a bottom surface;
   a toe portion;
   a heel portion;
   a leg portion, wherein the leg portion comprises a calf portion and a shin portion;
   a neck portion, wherein the neck portion connects the foot portion to the leg portion;
   a cuff portion, wherein the cuff portion is configured to be located at a terminal point of the leg portion;
   an inside surface and an outside surface;
   a first fabric, wherein the first fabric is located on the outside surface and is configured to exert pressure on portions of a user's foot and leg of between approximately eight and fifty millimeters of mercury; and
   a second fabric, wherein the second fabric is located on the inside surface, the second fabric further comprising cooling properties, wherein the cooling properties of the second fabric further comprise a moisture wicking component, wherein the moisture wicking component is configured to retain heat when activated by perspiration, the second fabric further comprising antimicrobial particles, wherein the antimicrobial particles are comprised of jade, wherein the antimicrobial particles comprised of jade are infused into the second fabric and the antimicrobial particles comprised of jade are configured to undergo a chemical or physical change when exposed to moisture, absorbing heat in the process.

2. A temperature variant stocking comprising:
   a foot portion, wherein the foot portion has a top surface and a bottom surface;
   a toe portion;
   a heel portion;
   a leg portion, wherein the leg portion comprises a calf portion and a shin portion;
   a neck portion, wherein the neck portion connects the foot portion to the leg portion;
   a cuff portion, wherein the cuff portion is configured to be located at a terminal point of the leg portion;
   a first fabric and a second fabric wherein the first fabric exerts a compressive force on portions of a user's foot and leg of between approximately eight and fifty millimeters of mercury; and
   the second fabric has a cooling element, or, in the alternative, the second fabric is a heat generating fabric, wherein the first fabric and the second fabric are knitted together in alternating strips creating a plurality of alternating strips, wherein the plurality of alternating strips are spaced apart from each other, are parallel to each other and run longitudinally from a first end of the leg portion to a second end of the leg portion of the compression stocking.

3. A method of making the temperature variant stocking of claim 1 comprising:
   selecting a first fabric, wherein selecting the first fabric further comprises assigning an outside surface to the temperature variant stocking, wherein the outside surface has properties that exert a pressure on portions of a user's foot and leg;
   selecting a second fabric wherein selecting the second fabric comprises assigning an inside surface to the temperature variant stocking, wherein the second fabric has properties that cool a user's skin, or wherein selecting a second fabric comprises assigning an inside surface to the temperature variant stocking, wherein the second fabric has properties that warm a user's skin;
   selecting an antimicrobial particle, wherein selecting an antimicrobial particle further comprises selecting an antimicrobial particle that is attachable to portions of the second fabric; and
   disposing all portions of a surface of the second fabric onto all portions of the inside surface of the temperature variant stocking.

* * * * *